United States Patent
Davidson

(10) Patent No.: US 10,265,515 B2
(45) Date of Patent: Apr. 23, 2019

(54) GALVANICALLY ASSISTED ANEURYSM TREATMENT

(71) Applicant: COVIDIEN LP, Mansfield, CA (US)

(72) Inventor: James Davidson, San Juan Capistrano, CA (US)

(73) Assignee: Covidien LP, Mansfield, MA (US)

( * ) Notice: Subject to any disclaimer, the term of this patent is extended or adjusted under 35 U.S.C. 154(b) by 154 days.

(21) Appl. No.: 14/671,217

(22) Filed: Mar. 27, 2015

(65) Prior Publication Data

US 2016/0279406 A1    Sep. 29, 2016

(51) Int. Cl.
| A61N 1/05 | (2006.01) |
| A61B 17/12 | (2006.01) |
| A61B 17/00 | (2006.01) |

(52) U.S. Cl.
CPC ........... *A61N 1/05* (2013.01); *A61B 17/1214* (2013.01); *A61B 17/12022* (2013.01); *A61B 17/12113* (2013.01); *A61B 2017/00831* (2013.01)

(58) Field of Classification Search
CPC .. A61B 2018/00404; A61B 2018/0041; A61B 18/1206; A61N 1/05
See application file for complete search history.

(56) References Cited

U.S. PATENT DOCUMENTS

| 5,904,651 A | 5/1999 | Swanson et al. |
| 6,015,424 A | 1/2000 | Rosenbluth et al. |
| 6,416,530 B2 | 7/2002 | DeVries et al. |
| 6,658,288 B1 | 12/2003 | Hayashi |
| 7,300,458 B2 | 11/2007 | Henkes et al. |
| 7,458,974 B1 | 12/2008 | Hayashi et al. |
| 7,985,252 B2 * | 7/2011 | Radhakrishnan ....... A61L 31/08 623/1.38 |
| 8,016,853 B2 | 9/2011 | Griffen et al. |

(Continued)

FOREIGN PATENT DOCUMENTS

| WO | 2009105710 A1 | 8/2009 |
| WO | WO-2009/105710 A1 | 8/2009 |

(Continued)

OTHER PUBLICATIONS

Duncan, et al., "On the treatment of aneurysm by electrolysis . . . ", Medico-Chir Soc Edinb Med J, 13, 1867, pp. 101-120.

(Continued)

*Primary Examiner* — Michael J D Abreu
(74) *Attorney, Agent, or Firm* — Fortem IP LLP; Matthew Lincicum

(57) ABSTRACT

Treatment of an aneurysm or other vascular defect can be facilitated or enhanced by a galvanic cell formed by an implantable medical device configured to be implanted at or within the aneurysm or other vascular defect. The implantable medical device can include a primary structure including an anodic metal and a cathodic metal. The anodic metal and the cathodic metal each form a fraction of a total surface area of the primary structure. A galvanic cell formed by the anodic metal and the cathodic metal is configured to induce a galvanic voltage within blood for a duration of time to promote thrombosis. The thickness of the anodic metal can be less than or equal to 5 μm, for example, to provide galvanic activity for between 5 and 30 minutes.

23 Claims, 12 Drawing Sheets

(56) References Cited

U.S. PATENT DOCUMENTS

| | | |
|---|---|---|
| 8,052,744 B2 | 11/2011 | Girton |
| 8,114,148 B2 | 2/2012 | Atanasoska et al. |
| 8,236,046 B2 | 8/2012 | Weber |
| 8,556,927 B2 | 10/2013 | Dehnad |
| 8,668,732 B2 | 3/2014 | Scheuermann et al. |
| 8,715,339 B2 | 5/2014 | Atanasoska et al. |
| 2002/0082679 A1 | 6/2002 | Sirhan et al. |
| 2002/0120297 A1* | 8/2002 | Shadduck ........ A61B 17/12022 607/2 |
| 2003/0217794 A1 | 11/2003 | Boylan et al. |
| 2005/0119723 A1 | 6/2005 | Peacock |
| 2005/0178584 A1 | 8/2005 | Wang et al. |
| 2006/0009798 A1* | 1/2006 | Callister .......... A61B 17/12022 606/200 |
| 2006/0122694 A1 | 6/2006 | Stinson et al. |
| 2006/0271169 A1 | 11/2006 | Lye et al. |
| 2006/0293706 A1 | 12/2006 | Shimon |
| 2007/0270942 A1* | 11/2007 | Thomas .................. A61F 2/07 623/1.46 |
| 2008/0058919 A1 | 3/2008 | Kramer-Brown et al. |
| 2008/0071350 A1 | 3/2008 | Stinson |
| 2008/0082162 A1 | 4/2008 | Boismier et al. |
| 2008/0262489 A1 | 10/2008 | Steinke |
| 2009/0149947 A1 | 6/2009 | Frohwitter |
| 2009/0248060 A1 | 10/2009 | Schneider et al. |
| 2010/0008970 A1 | 1/2010 | O'Brien et al. |
| 2010/0145380 A1 | 6/2010 | Quandt et al. |
| 2011/0060212 A1 | 3/2011 | Slee et al. |
| 2011/0160763 A1 | 6/2011 | Ferrera et al. |
| 2011/0238153 A1 | 9/2011 | Atanasoska et al. |
| 2011/0282428 A1 | 11/2011 | Meyer et al. |
| 2011/0301594 A1 | 12/2011 | Orion |
| 2011/0307034 A1* | 12/2011 | Hastings ............ A61B 18/1206 607/61 |
| 2012/0083868 A1 | 4/2012 | Shrivastava et al. |
| 2013/0066359 A1 | 3/2013 | Murphy et al. |
| 2013/0072960 A1 | 3/2013 | Schneider et al. |
| 2013/0096606 A1 | 4/2013 | Bruchman et al. |
| 2014/0018844 A1 | 1/2014 | Dehnad |
| 2014/0031858 A1 | 1/2014 | Bhagchandani et al. |
| 2014/0163604 A1 | 6/2014 | Monstadt |
| 2014/0194911 A1 | 7/2014 | Johnson et al. |
| 2014/0194919 A1 | 7/2014 | Losordo et al. |
| 2015/0080937 A1 | 3/2015 | Davidson |
| 2015/0133990 A1 | 5/2015 | Davidson |
| 2015/0297803 A1 | 10/2015 | Pulugurtha |

FOREIGN PATENT DOCUMENTS

| | | |
|---|---|---|
| WO | 2012044757 A1 | 4/2012 |
| WO | 2013071173 A1 | 5/2013 |
| WO | WO-2013/071173 A1 | 5/2013 |
| WO | WO-2013142756 | 9/2013 |
| WO | 2014041428 A1 | 3/2014 |
| WO | WO-2014/041428 A2 | 3/2014 |

OTHER PUBLICATIONS

Piton, et.al., "Vascular thrombus induced by direct electric current", Neuroradiology, 16, 1, 1978, pp. 385-388.

Schumacher, et.al., "A ferret model of electrical-induction of arterial thrombosis that is sensitive to aspirin", J. Pharm. & Tox Methods, 35, 1, 1996, pp. 3-10.

Shih, "Galvanic current induced heterogeneous structures on stainless steel wire", Cor. Sci., 47, 8, 2005, pp. 2199-2212.

Siddique, et al., "Treatment of aneurysms with wires and electricity: a historical overview", J. Neurosurg., 99, 2003, pp. 1102-1107.

International Search Report and Written Opinion for International Application No. PCT/US2016/023861, dated Jul. 6, 2016, 14 pgs.

* cited by examiner

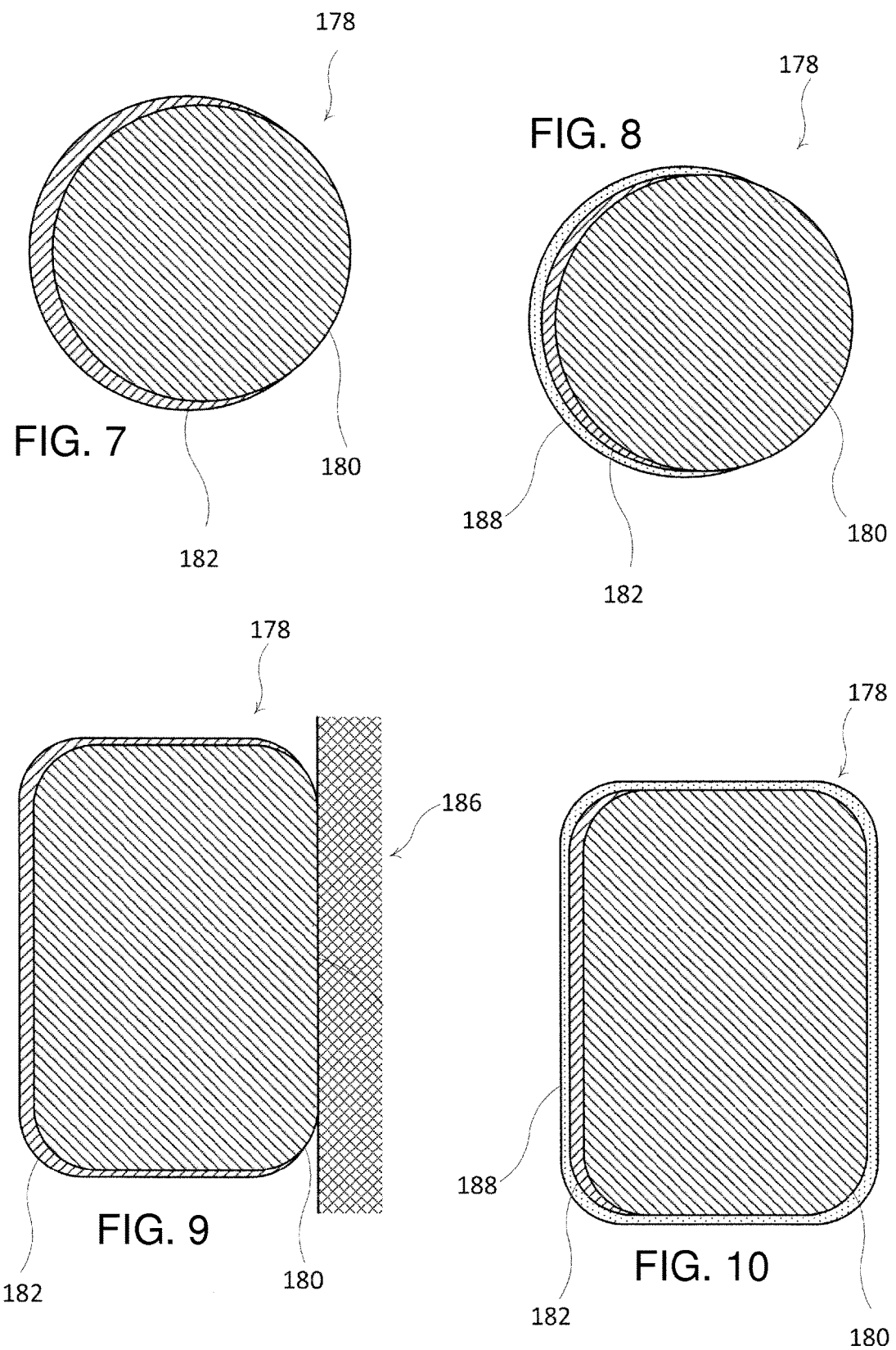

GALVANICALLY ASSISTED ANEURYSM TREATMENT

BACKGROUND

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms could be found in different parts of the body; the most common being abdominal aortic aneurysms (AAA) and the brain or cerebral aneurysms. The mere presence of an aneurysm is not always life-threatening, but they can have serious health consequences such as a stroke if one should rupture in the brain. Additionally, a ruptured aneurysm can also result in death.

Endovascular techniques can be employed for the implantation of medical devices for the treatment and occlusion of body cavities such as arteries, veins, fallopian tubes or vascular deformities. For example, occlusion of vascular aneurysms can be performed using an implantable device, such as an intrasaccular implant, that is introduced with the aid of an endovascular delivery wire through a catheter. Once moved to the treatment site, the intrasaccular implant can be moved into the aneurysm cavity to occlude the aneurysm.

SUMMARY

An aspect of at least some of the embodiments disclosed herein involves the recognition that a galvanically induced electrical charge can assist treatment and thrombus formation within an aneurysm and thereby reduce risk of rupture at the aneurysm. The electrical charge generated by a galvanic couple can cause or increase thrombosis at or near one or more of the metals in the galvanic couple and the thrombotic material.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 16, 20, 25, 26, or 27. The other clauses can be presented in a similar manner.

1. An implantable medical device configured to be implanted within a body, the device comprising:
    a primary structure including an anodic metal and a cathodic metal, the anodic metal and the cathodic metal each forming a fraction of a total surface area of the primary structure;
    wherein a thickness of the anodic metal is less than or equal to 5 µm, and a galvanic cell formed by the anodic metal and the cathodic metal is configured to induce a galvanic voltage within blood within the body for between 5 and 30 minutes.

2. The implantable medical device of Clause 1, wherein the fraction of the surface area formed by the anodic metal is located primarily at an internal aspect of the implant.

3. The implantable medical device of Clause 1, wherein 35% to 85% of the surface area of the primary structure is formed by the anodic metal.

4. The implantable medical device of Clause 1, wherein the fraction of the total surface area formed by the anodic metal comprises a plurality of discrete portions of the anodic metal.

5. The implantable medical device of Clause 1, wherein the fraction of the surface area formed by the anodic metal is contiguous.

6. The implantable medical device of Clause 1, wherein the anodic metal is in direct contact with the cathodic metal.

7. The implantable medical device of Clause 1, wherein at least a portion of the anodic metal has a thickness of at least 1 m.

8. The implantable medical device of Clause 1, wherein the anodic metal comprises magnesium and the cathodic metal comprises nickel and titanium.

9. The implantable medical device of Clause 1, wherein the primary structure forms a helical coil.

10. The implantable medical device of Clause 9, further comprising:
    a stretch-resistant member extending within a lumen formed by the helical coil; and
    at least one fiber attached to the helical coil and extending outwardly from a central axis of the helical coil.

11. The implantable medical device of Clause 1, wherein the primary structure forms a braided ball.

12. The implantable medical device of Clause 1, further comprising a temporary cover material that encapsulates at least a portion of the anodic metal.

13. The implantable medical device of Clause 12, wherein the temporary cover material is erodible, dissolvable, degradable or absorbable in vivo.

14. The implantable medical device of Clause 13, wherein the temporary cover material encapsulates substantially all of the anodic metal.

15. The implantable medical device of Clause 1, wherein the galvanic cell is configured to induce a galvanic voltage within blood within the body for between 5 and 30 minutes, and no longer.

16. A method, comprising:
    inserting an implantable medical device into a space within a body, the medical device comprising:
    a primary structure including an anodic metal and a cathodic metal, the anodic metal and the cathodic metal each forming a fraction of a total surface area of the primary structure, wherein a thickness of the anodic metal is less than or equal to 5 µm;
    galvanically assisting thrombosis within the space with a galvanic cell formed by the anodic metal and the cathodic metal by inducing a galvanic voltage within blood within the body for between 5 and 30 minutes.

17. The method of Clause 16, wherein the galvanic cell is activated while the implantable medical device is within an aneurysm within the body.

18. The method of Clause 16, wherein galvanically assisting thrombosis comprises binding, through a galvanic reaction, blood constituents to an anode of the galvanic cell.

19. The method of Clause 16, wherein inducing a galvanic voltage within blood within the body for between 5 and 30 minutes, comprises doing so for between 5 and 30 minutes, and no longer.

20. An implantable medical device configured to be implanted within a body, the device comprising:
    a primary structure configured to occupy a space within the body;

means for inducing a galvanic voltage between an anodic metal and a cathodic metal of the primary structure while within blood of the body, to galvanically assist thrombosis within the body for between 5 and 30 minutes.

21. The implantable medical device of Clause 20, wherein the means for galvanically assisting thrombosis within the body comprises an anodic metal and a cathodic metal.

22. The implantable medical device of Clause 21, wherein a thickness of the anodic metal is less than or equal to 5 µm.

23. The implantable medical device of Clause 21, wherein the anodic metal comprises magnesium and the cathodic metal comprises nickel and titanium.

24. The implantable medical device of Clause 20, wherein said means comprises means for inducing a galvanic voltage between an anodic metal and a cathodic metal of the primary structure while within blood of the body, to galvanically assist thrombosis within the body for between 5 and 30 minutes, and no longer.

25. An implantable medical device configured to be implanted within a body, the device comprising:
   a primary structure including an anodic metal and a cathodic metal, the anodic metal and the cathodic metal each forming a fraction of a total surface area of the primary structure;
   wherein a thickness of the anodic metal is such that a galvanic cell formed by the anodic metal and the cathodic metal is configured to induce a galvanic voltage within blood within the body for a duration of time to enable partial or complete thrombus formation within the body.

26. A method, comprising:
   inserting an implantable medical device into a space within a body, the medical device comprising:
   a primary structure including an anodic metal and a cathodic metal, the anodic metal and the cathodic metal each forming a fraction of a total surface area of the primary structure;
   galvanically assisting thrombosis within the space with a galvanic cell formed by the anodic metal and the cathodic metal by inducing a galvanic voltage within blood within the body for a duration of time to enable partial or complete thrombus formation within the body.

27. An implantable medical device configured to be implanted within a body, the device comprising:
   a primary structure configured to occupy a space within the body;
   means for inducing a galvanic voltage between an anodic metal and a cathodic metal of the primary structure while within blood of the body, to galvanically assist thrombosis within the body for a duration of time to enable partial or complete thrombus formation within the body.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 7, 8, 9, 10, 11, and 12 are schematic cross-sections of filaments, according to various embodiments.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details. For example, although some drawings show the implementation of a galvanic effect in embodiments of an intrasaccular implant, the present disclosure encompasses the implementation of a galvanic effect in other endovascular devices, or in any implant, and/or for assisting aneurysm treatment. In some instances, well-known structures and components are shown in block diagram form in order to avoid obscuring the concepts of the subject technology.

The subject technology can provide a galvanic reaction that facilitates thrombosis at a target site. For example, an interior body of an aneurysm may undergo progressive thrombosis and substantially stop flow of blood within the aneurysm at least in part due to the galvanic reaction. Galvanic activity can also facilitate rapid thrombosis at the ostium of the aneurysm to reduce or prevent flow into or out of the aneurysm. Subsequently, further thrombosis within the aneurysm can be accelerated once flow has ceased and the blood remains stagnant. According to some embodiments, substantial thrombosis can be more readily achieved within an aneurysm at the target site through galvanic reactions provided by the implant. Where certain conditions relating to the implant are required to achieve substantial thrombosis without galvanic reactions, such requirements can be at least partially alleviated by the galvanic activity disclosed herein. Furthermore, the structure and arrangements to achieve such galvanic reactions can be provided with little or no interference with other structural and functional features of the implant, such as an ability to recover a shape memory configuration.

In one or more embodiments, the systems and devices disclosed herein may be used in veterinary or human medicine and, more particularly, for the endovascular treatment of intracranial aneurysms and acquired or innate arteriovenous blood vessel malformations and/or fistulas and/or for the embolization of tumors by thromboembolization. For this purpose, components of the various systems and devices disclosed herein may be designed as a coil implant, a spherical implant, a stent, a filter, and the like, but may as well possess any other superimposed configuration as may be expedient. In one or more embodiments, the systems and devices disclosed herein may provide various designs and configurations for an aneurysm implant, as especially appropriate for the occlusion of intracranial aneurysms.

Figure 1A:
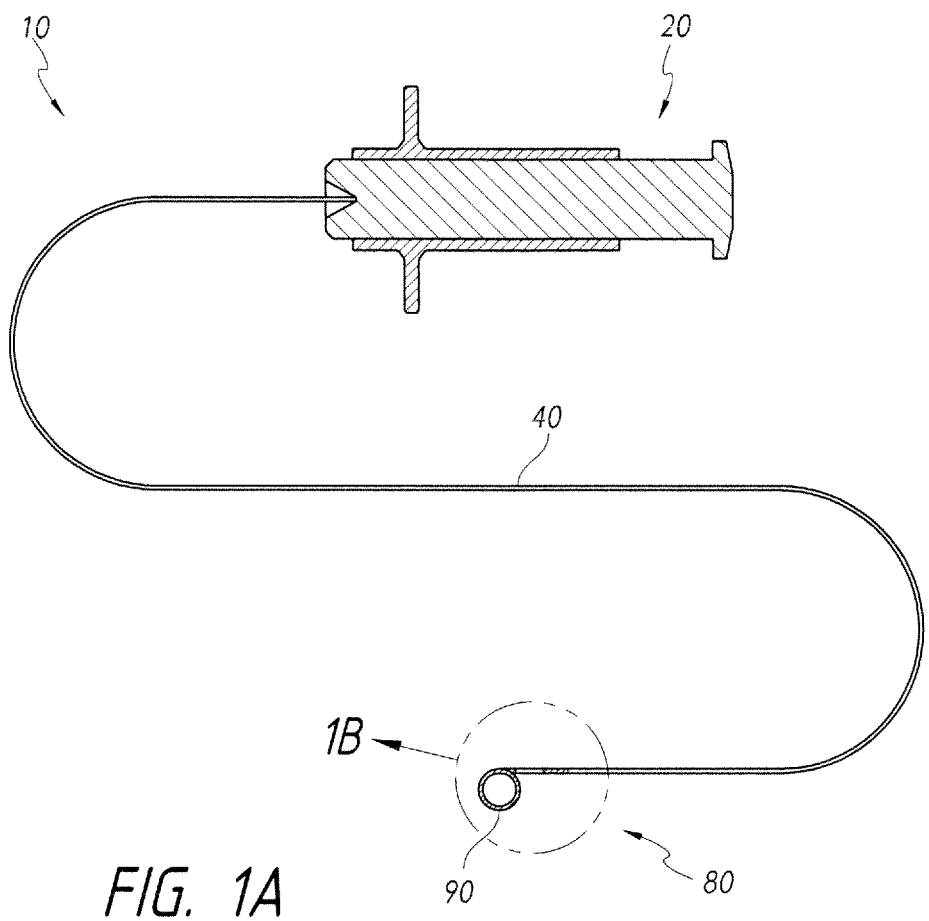
FIG. 1A shows a plan view of the positioning system in accordance with some embodiments of the subject technology, and a plan view of an exemplary implant in accordance with some embodiments of the subject technology.
Figure 1B:
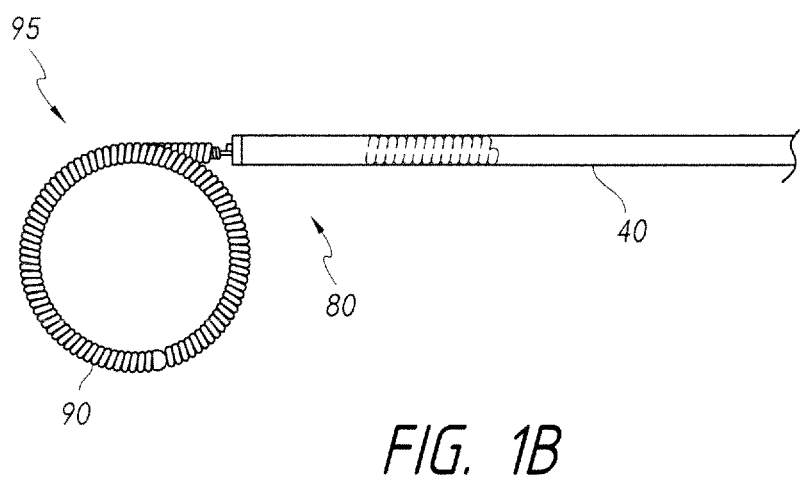
FIG. 1B shows a closer view of a portion of FIG. 1A.

A vascular implant device may be a positioning system 10 such as the one shown in FIGS. 1A-1B. The positioning system 10 shown in FIGS. 1A-1B can include an actuator 20, a positioner 40 coupled with the actuator 20, and an implant interface 80 at the distal portion of the positioner 40. A portion of the implant interface 80 may engage a complementary portion of an implant 95 in order to control the delivery (i.e., securing and detaching) of the implant 95 at the desired location. While the implant is shown or described in several embodiments as comprising an embolic coil 90, any implant or device that is compatible with the subject technology may be used in lieu of or in conjunction with the coil 90 in accordance with the embodiments described herein. Suitable implants and devices include, but are not limited to, stents, filters, thrombectomy devices, atherectomy devices, flow restoration devices, embolic coils, spherical devices, embolic protection devices, or other devices, and the like. Moreover, it will be appreciated that both detachable and non-detachable implants and/or devices may be used.

Referring again to FIGS. 1A-1B, the implant interface 80 is a portion of the positioning system 10 that allows the operator to control the engagement and disengagement of the implant 95 to the positioner 40, and allows the positioner 40 to retain the implant 95 in a way that minimally contacts the implant 95, that permits movement of the implant relative to the positioner in some or all of axial, tilt, and rotational directions, and that allows the implant 95 to move axially and without radial movement when engaging and disengaging the implant interface 80.

Figure 1C:
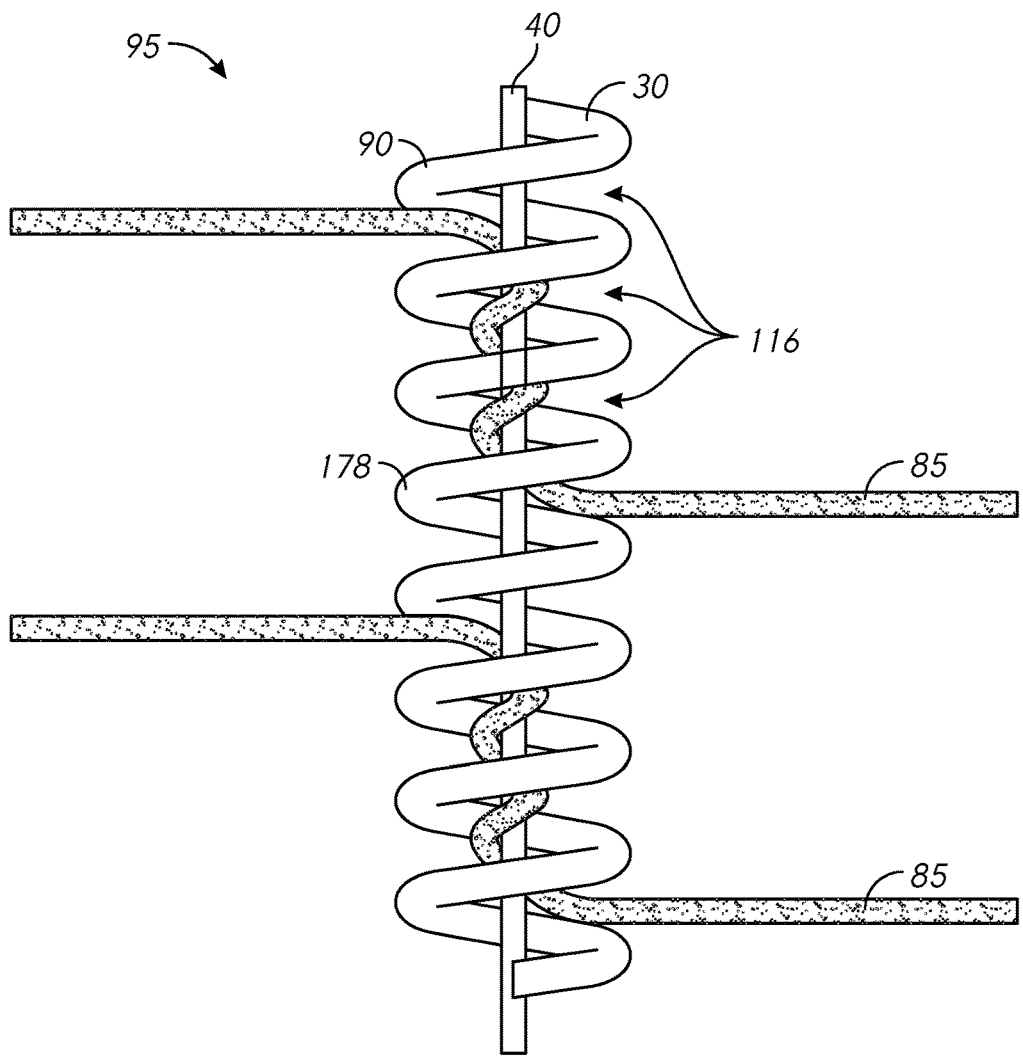
FIG. 1C illustrates one embodiment, in plan view, an exemplary wrapping pattern of the fibers around the stretch resistant member.
Figure 1D:
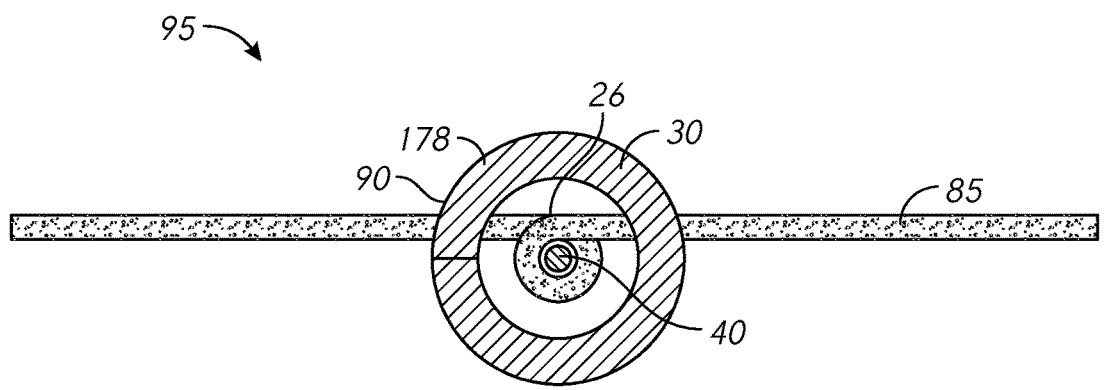
FIG. 1D is a cross-sectional view of the wrapping pattern of the fibers around the stretch-resistant member shown in FIG. 1C.

According to some embodiments, the implant 95 illustrated in FIGS. 1C-1D can include a primary coil 30, a stretch-resistant member 40, and one or more fibers 85. Additional coils can also be included within, about, or between windings of the primary coils 20. The additional coils can have the same or different wire diameters, the same or different winding directions, and the same or different winding pitch angles. The primary coil 30 has a proximal portion and a distal portion defining an internal lumen 26 extending between the ends of the primary coil 30. Openings 116 can be formed between portions of the primary 20, wherein the openings connect the internal lumen 26 to an exterior of the primary coil 30. The primary coil 30 can be formed in a variety of shapes once heat setting of the coil form is performed. The fiber(s) 85 can be a plurality of fibers, at least one bundle of fibers, or a plurality of fiber bundles. The fiber(s) 85 can be enlaced, tied, or knotted to a number of places on the implant 95. The fibers or fiber bundles 85 can be disposed so that they are not tied or knotted to the implant 95, thereby avoiding potentially obstructive bundles that might hinder deployment of the implant 95 or might mechanically damage the implant 10. The use of fibers with coils is disclosed in U.S. Publ. No. 2006/0036281, U.S. Publ. No. 2008/0228215, U.S. Publ. No. 2008/0103585, and U.S. Pat. No. 7,896,899, which are incorporated by reference in their entirety. In one embodiment illustrated in FIGS. 1C-1D, the fiber 85 is wrapped at least one or two times around the stretch-resistant member 40. In another embodiment, the fiber(s) 85 are enlaced through a pair of loops of the primary coil 30. In yet another embodiment, the fiber(s) 85 are enlaced in an "S" pattern through a plurality of loops in the primary coil 30. In still yet another embodiment, the fiber(s) 85 are enlaced adjacent to each other in an "S" pattern on the primary coil 30. The stretch-resistant member 40 and fibers/fiber bundles 85 are preferably made of polymeric materials. The polymeric materials can be nonbiodegradable polymers such as polyethylene, polyacrylics, polypropylene, polyvinylchloride, polyamides such as nylon, e.g., Nylon 6.6, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. The polymeric materials can be biodegradable materials, such as polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polylactic acid (PLA), polyglycolic acid (PGA), poly(p-dioxanone), poly (valerolactone), poly(tartronic acid), poly($\beta$-malonic acid), poly(propylene fumarate), poly(anhydrides), and tyrosine-based polycarbonates.

Figure 2A:
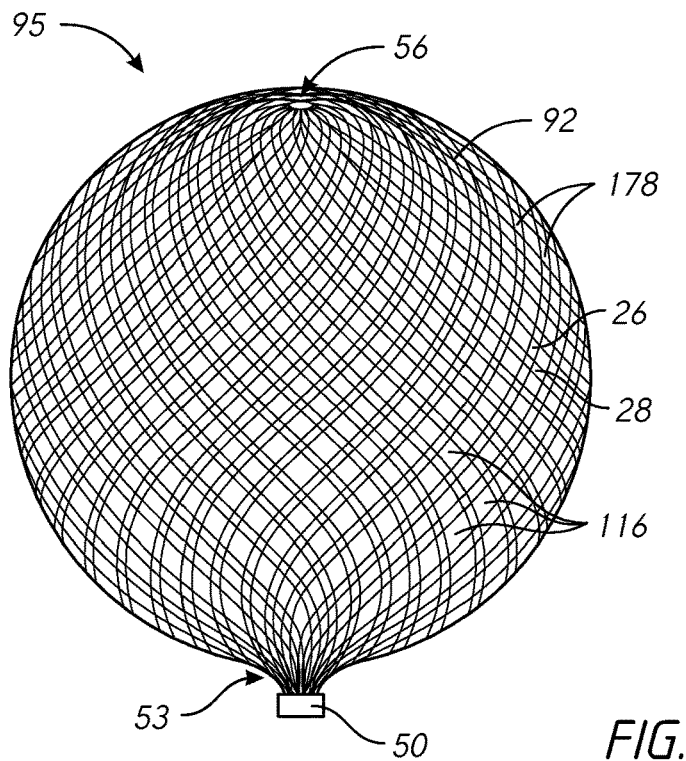
FIG. 2A shows a perspective side view of a braid ball, in accordance with one or more embodiments of the present disclosure.
Figure 2B:
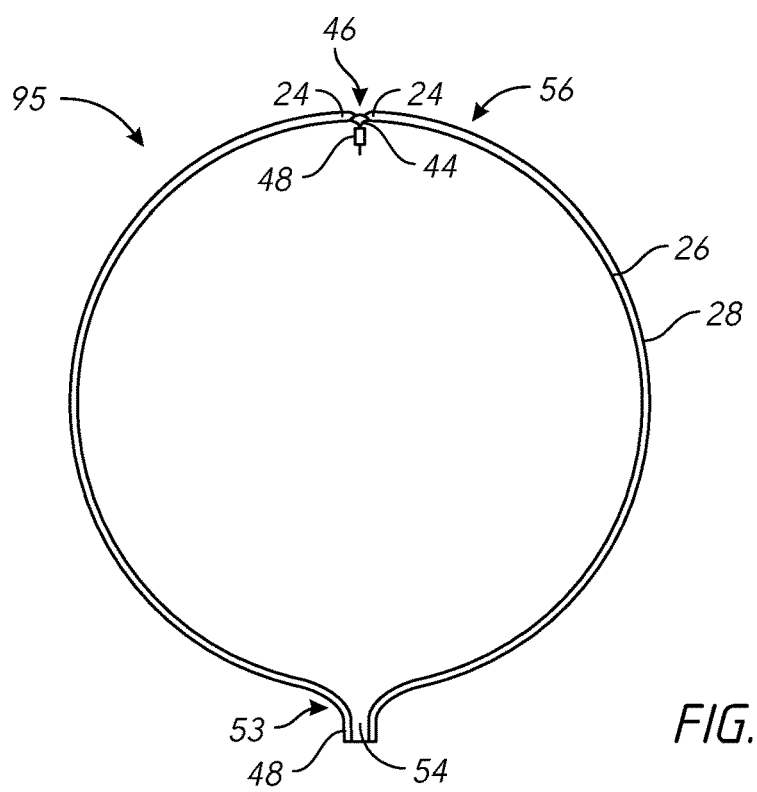
FIG. 2B shows a side-sectional view of a braid ball implant deployed within a bifurcation aneurysm, in accordance with one or more embodiments of the present disclosure.

According to some embodiments, as shown in FIGS. 2A-2B, an implant 95 delivered by the system 10 can be or include a braid ball 92. The braid ball 92 can be formed from tubular braid stock including a resilient material, such as Nitinol, that defines an open volume (generally round, spherical, ovular, heart-shaped, etc.) in an uncompressed/ unconstrained state. The size of the implant 95 can be selected to fill an aneurysm at the target site 16, so the proximal portion 53 of the device helps direct blood flow along the surface of the braid from which it is constructed. A distal portion 56 of the ball can be dome-shaped. The braid ball 92 can include a single layer or two layers 26, 28 (inner and outer layer, respectively) construction at least where impacted by flow against the aneurysm. Openings 116 can be formed between filaments of the layers 26, 28, wherein the openings connect an interior region of the braid ball 92 to an exterior of the braid ball 92. As shown, one or more turns of a coil (e.g., Pt wire) or a band (not shown) can provide a distal radiopaque feature to mark the location of the braid ball 92. Some exemplary implants that can be used in conjunction with the systems described herein are disclosed at U.S. Pub. No. 2013/0123830, published on May 16, 2013, the entirety of which is incorporated herein by reference.

According to some embodiments, the implant 95 can include a hub 50 at a proximal portion 53 thereof. The hub 50 can be fixedly attached to the remainder of the implant 95. For example, the hub 50 can grasp braided filaments of the layers 26, 28 of the implant 95. According to some embodiments, the implant 95 can be set within an aneurysm sac at the target site 16 forming a vascular bifurcation.

According to some embodiments, as shown in FIG. 2B, A distal end of the ball can be dome-shaped adjacent a fold 24 in the braid resulting in the two-layers 26, 28 (inner and outer layer, respectively). The braid ball 92 can include a tie 44 closing an aperture 46 defined by the fold 24. A radiopaque (e.g., Pt) marker 48 can be held by the tie 44. Radiographic visibility of the proximal end of the ball may be achieved by virtue of the density of the braid coming together, alone, or a radiopaque (e.g., Pt) band 50 may be added. Tie 44 may comprise any biocompatible material including Stainless Steel, Titanium, Nitinol (possibly wire that is martinistic at body temperature commonly referred to as "muscle wire"), suture, etc. According to some embodiments, a flared or trumpet-shaped recapture profile is set in the braid to aid in device recapture into the delivery catheter through which the device is advanced. An access port 54 can be provided within the hub. The port 54 accepts a delivery system interface. Delivery system construction as well as further optional details of the braid ball 92 are provided below.

When set within an aneurysm, the braid ball 92 can substantially conform to its shape. Generally, the braid ball 92 can be oversized somewhat to exert some small load on the aneurysm wall to help maintain a stable position of the ball. However, the ball may be intentionally undersized, especially in a side-wall application should it be desired that any hub feature is able to turn with the ball to trail with the blood flow. Braid filaments are shown in pairs within the braid ball 92—one from each layer 26, 28. While the organization of the braid is often more random, the double/dual layer construction—on average—results higher density that might be achieved with a single-layer braid ball 92 due to limitations on braid density for a given starting diameter of braid.

While the implant 95 can be an embolic coil 90 or a braid ball 92 as illustrated herein, the implant 95 can have any other form or structure, according to various embodiments. For example, the implant 95 can be a cylindrical, tube-like stent, or a filter. Other types of implants and treatment devices are generally known. The subject technology can be applied to any such implant or treatment device for delivery and implantation.

In some embodiments, the implant 95 can comprise metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium (Mg) alloys, polylactic acid, poly glycolic acid, poly ester amide (PEA), poly ester urethane (PEU), amino acid based bioanalogous polymers, tungsten, tantalum, platinum, polymers, bio-polymers, ceramics, bio-ceramics, or metallic glasses. In some embodiments, the implant 95 may be formed from materials having shape memory properties. Where a galvanic effect is desired, the implant 95 should be formed from metal, or from a non-metal that is coated or otherwise covered partially or wholly with metal.

In some embodiments, the implant 95 can have a galvanic cell or a plurality of galvanic cells formed by a portion or on a surface thereof. Such galvanic cell(s) can generate, in the presence of blood, thrombus, or other electrolytic medium, a voltage and/or electrical charge that promotes thrombosis at a target site 16. For example, the galvanic cell(s) can generate an electrical charge, or electrically charged region(s), on the implant 95 that can generate, promote, attract, adhere, and/or attach thrombus to the implant 95 or otherwise within or near the target site 16 when the implant 95 is deployed next to or into the target site 16. The generated charge or charged regions on the implant 95 can have a charge opposite that of constituents (e.g., blood constituents) of or at the target site 16. The generated charge or charged regions can include both regions of negative charge and regions of positive charge, each of which can generate, promote, attract, adhere, and/or attach to blood constituents or thrombus constituents of the opposite charge. The generation, promotion, attraction, adhesion, and/or attachment of blood constituents within the target site 16 may be electrostatic.

The galvanic cell(s) can comprise at least two different metals (as used herein, "metal" can refer to a substantially pure or elemental metal, or to alloys), such as a first metal 180 and a second metal 182, that generate an electrical charge in the presence of an electrolytic medium, for example, such as blood. The metals may be characterized as having different reduction potentials or electrode potentials; various metal combinations may be determined with reference to the electromotive force (EMF) chart. The metals of the galvanic cell are in electrical contact, e.g., direct physical contact, with each other. The first metal 180 and second metal 182 can be selected to induce a galvanic voltage and impart a desired charge arrangement in a galvanic region. For example, the metals 180, 182 can be selected so that the first metal 180 functions as a cathode (having a positive charge) and the second metal 182 functions as an anode (having a negative charge), or vice versa. Any combination of anode and cathode metals can be employed. One useful combination is a first metal of nickel-titanium alloy, e.g., nitinol, or a platinum-tungsten alloy, and a second metal e.g. of magnesium, in which case the first metal can act as a cathode and as the structural metal of the implant 95, and the second metal can act as an anode. The reverse can be employed as well, in which the first metal is magnesium and the second metal is nitinol.

In a single cell the nitinol-magnesium combination, for example, can induce a galvanic voltage of about 1.3 volts in saline. Other strongly anodic metals can be used as a first or second metal in combination with nitinol, for example lithium or zinc. Metals other than nitinol also can be used as a cathode, such as, for example, platinum, nickel, titanium, gold, graphite, and silver. The structural metal of the implant 95 can also be employed as anode, where a metal that is cathodic relative to the structural metal is employed as the second metal. In a single implant 95, multiple types of first metals and/or multiple types of second metals can be employed. For example, one second metal type can be employed in one portion of the implant 95 and another second metal type can be employed in another portion of the implant 95. Metal combinations other than nitinol-magnesium may induce galvanic voltages different than does nitinol-magnesium. For example, a galvanic cell comprising nitinol and platinum can induce a galvanic voltage of about 0.49 volts in saline. A galvanic cell comprising magnesium and nitinol can induce a galvanic voltage of about 1.3 volts in saline. A galvanic cell comprising magnesium and platinum can induce a galvanic voltage of about 1.7 volts in saline. A galvanic cell comprising lithium and nitinol can induce a galvanic voltage of about 2.7 volts in saline. A galvanic cell comprising lithium and platinum can induce a galvanic voltage of about 3.1 volts in saline.

FIGS. 3-6 illustrate several embodiments of the implant 95, or a portion thereof, that include one or more galvanic cells. Such cells can be formed by providing a first metal 180 and a second metal 182 disposed over and in electrical contact, e.g., direct physical contact, with the first metal 180. The first metal 180 can comprise, for example, the metal from which the implant 95 is fabricated. For example, with respect to an embolic coil 90, the first metal 180 can comprise the primary coil 30 of the embolic coil 90. By further example, with respect to a braid ball 92, the first metal 180 can comprise the layers 26,28 of the braid ball 92. For example, the embolic coil 90 or the braid ball 92 can be formed, at least in part, from filaments 178 of the first metal 180. For convenience herein, the filaments 178 of such a metal can be considered the "structural metal" of the implant 95. The first metal 180 can alternatively comprise a metal which is plated, coated, deposited, or otherwise applied over some or all of the structural metal (or structural polymer) of the implant 95.

The second metal 182 can be coated, deposited, welded, plated, or otherwise applied over some or all of the structural metal (or structural polymer where a metal-coated polymer is employed) of the implant 95, which may be the first metal 180 or another metal. If the first metal 180 comprises a metal which is plated, coated, deposited, or otherwise applied over some or all of the structural metal (or structural polymer) of the implant 95, the second metal 182 can comprise the structural metal of the implant 95 or can be plated, coated, deposited, or otherwise applied over some or all of the structural metal (or structural polymer), which is neither the first metal nor the second metal.

As seen in FIGS. 3-6, the second metal 182 can be arranged in an intermittent pattern of one or more discrete second metal regions on a region of the first metal 180 (or alternatively in a continuous layer over at least a portion of the first metal 180). One or more portions of the structural metal (or structural polymer) can be masked or otherwise covered (e.g., by a mandrel 186), for example as illustrated in FIG. 9, during plating, coating, deposition, or other application of the first metal, the second metal, or both on the structural metal (or structural polymer). The region of the first metal 180 can be continuous or generally continuous, including any portions thereof that underlie the second metal 182 regions. Accordingly, a galvanic region of the implant 95 can comprise a pattern of one or multiple discrete second metal 182 regions situated on or in a first metal 180 region, which first metal region can be continuous or generally continuous in the area(s) in which the galvanic region prevails. The galvanic region can prevail, for example, over the entire outer surface of the implant 95, or over a selected portion thereof, such as a proximal portion 53 and/or a distal portion 56 (see FIGS. 2A-2B). The galvanic region can prevail, for example, over any one or combination of the following: (a) some or all of a portion of a surface of the implant 95 that faces radially outwardly, away from a central longitudinal axis of the implant 95, (b) some or all of a portion of a surface of the implant 95 that faces radially inwardly, toward the central longitudinal axis of the implant 95, and (c) some or all of the portion of a surface of the implant 95 that faces laterally toward another portion of the implant 95, or otherwise. Instead of or in addition to the foregoing, the galvanic region can be configured such that one, some or all filament(s) 178, can have more than 1, 2, 3, 5, or 10 galvanic cells positioned on it.

Figure 4:
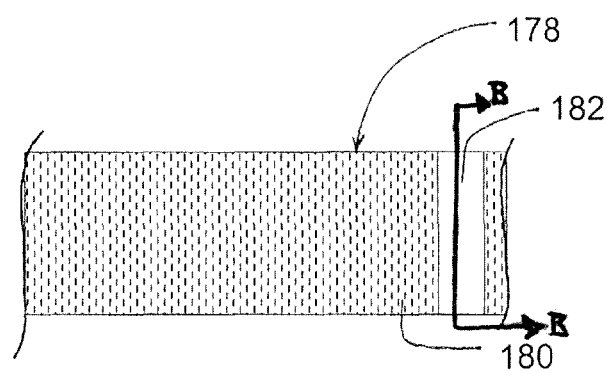

The locations (a), (b), and (c) are illustrated with respect to a single filament in FIGS. 7-10, which are schematic cross-sections of filaments 178, for example as taken along line B-B in FIG. 4. Each of the right and left directions in FIGS. 7-10 can be considered alternatively radially inward or outward. Accordingly, FIGS. 7-10 illustrate filaments having the first metal 180 prevailing over location (a) or (b) and the second metal 180 prevailing over the other of location (a) or (b). In FIGS. 7 and 9, the second metal 182 also extends onto the location (a) or (b) on which the first metal 180 prevails, but the extension of the second metal on to such location is to a much smaller degree such that such location is substantially free of the second metal. In FIGS. 8 and 10, the second metal 182 does not extend onto the location (a) or (b) on which the first metal 180 prevails, such that such location is free of the second metal. FIGS. 7-10 also illustrate the filaments 178 having the first metal 180 and the second metal 180 over location (c), although in different proportions. Thus, location (c) may overlap somewhat with locations (a) and/or (b) depending on the shape of the filament.

In a single implant 95 employing multiple types of first metals and/or multiple types of second metals, (i) one first metal type can be employed in one portion of the implant 95 (e.g., one of the locations (a), (b), (c) specified above) and another first metal type can be employed in another portion of the implant 95 (e.g., another of the locations (a), (b), (c)), and/or (ii) one second metal type can be employed in one portion of the implant 95 (e.g., one of the locations (a), (b), (c) specified above) and another second metal type can be employed in another portion of the implant 95 (e.g., another of the locations (a), (b), (c)).

Figure 3:
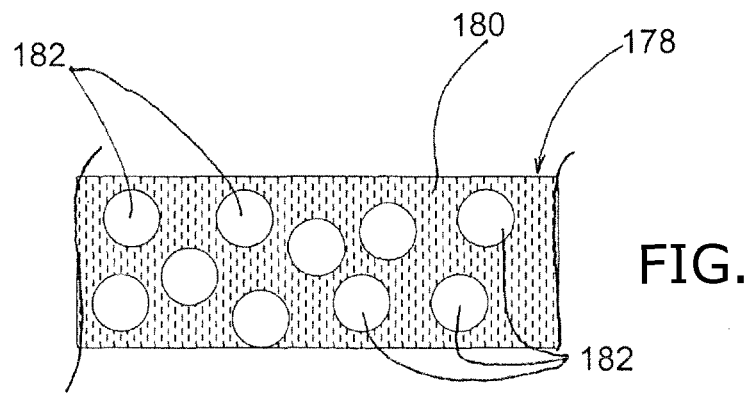
FIGS. 3, 4, 5, and 6 are schematic plan views of various embodiments of galvanic regions for use with the endovascular devices of FIGS. 1A-2B.
Figure 5:
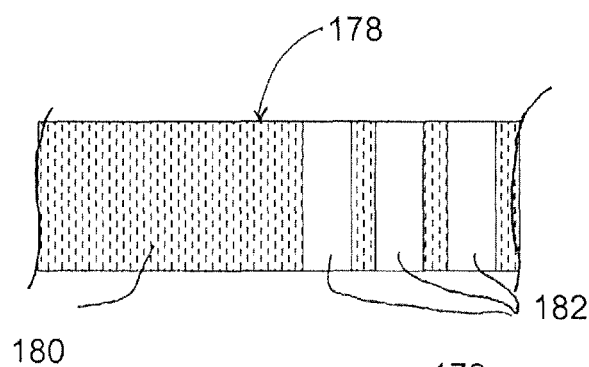
Figure 6:
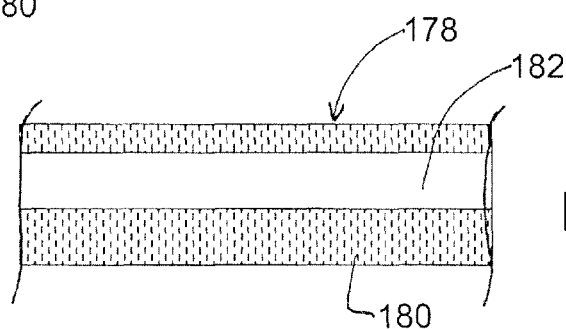

FIGS. 3-6 illustrate several embodiments that implement an intermittent pattern of discrete second metal regions 182, each in the context of a single filament 178 that can form one side of an opening wherein (for example) one or more filaments 178 border some or all openings 116. One, some or all of the filaments 178 bordering an opening 116 can have any of the patterns shown in FIGS. 3-6, or other intermittent pattern(s). FIG. 3 shows a pattern in which second metal regions 182 in the form of circular disks, polygons or other shapes are distributed in a (regular or random) spotted pattern in the first metal region 180. The disks, polygons, etc. can be of uniform or non-uniform size and/or shape. FIG. 4 shows a single second metal region 182 in the shape of a ring or band that can extend partially or completely around a filament 178. FIG. 5 shows a pattern that is similar to that of FIG. 4 but with multiple such rings or bands. FIG. 6 shows a pattern in which the second metal region 182 can take the form of one or more strips that extend longitudinally along the filament 178. Generally, the thickness of the second metal can be adjusted to increase or decrease the duration of the galvanic reaction.

In some embodiments, the second metal 182 can prevail in or cover some or all of the portion of the outer surface of the implant 95 that faces radially outwardly, away from the central longitudinal axis of the implant 95. For example, the second metal 182 can cover most or substantially all of such outward-facing surface of the implant 95, or most or substantially all of such outward-facing surface of the proximal portion 53 and/or the distal portion 56. In various embodiments, the second metal can cover at least 50%, at least 60%, at least 75%, at least 90%, at least 95%, or at least 98% of any such outward-facing surface of the implant 95. Additionally or alternatively, substantially all of such outward-facing surface of the implant 95 can be covered collectively by the second metal 182 in some areas and by some material other than the first metal 180 in other areas. In combination with any of the foregoing, the first metal 180 can cover, prevail in or be exposed in some or all of the portion of the outer surface of the implant 95 that faces radially inward, toward the central longitudinal axis of the implant 95. In the embodiments under discussion in this paragraph, the first metal can prevail substantially only on the inward-facing surface, and the second metal can prevail substantially only on the outward-facing surface, of the implant 95. In some embodiments, at least 50%, at least 60%, at least 75%, at least 90%, at least 95%, or at least 98% of a total surface area of the second metal can be at the outward-facing surface of the implant 95. In some embodiments, at least 50%, at least 60%, at least 75%, at least 90%, at least 95%, or at least 98% of a total surface area of the first metal can be at the inward-facing surface of the implant 95. In some embodiments, the first metal can be substantially absent from the outward-facing surface, and/or the second metal can be substantially absent from the inward-facing surface, of the implant 95. In some embodiments, less than 50%, less than 40%, less than 25%, less than 10%, less than 5%, or less than 2% of a total surface area of the second metal can be at the inward-facing surface of the implant 95. In some embodiments, at least 50%, at least 60%, at least 75%, at least 90%, at least 95%, or at least 98% of a total surface area of the second metal can be at other than the inward-facing surface of the implant 95. In some embodiments, less than 50%, less than 40%, less than 25%, less than 10%, less than 5%, or less than 2% of a total surface area of the first metal can be at the outward-facing surface of the implant 95. In some embodiments, at least 50%, at least 60%, at least 75%, at least 90%, at least 95%, or at least 98% of a total surface area of the first metal can be at the other than the outward-facing surface of the implant 95.

In some embodiments, the second metal 182 can prevail in or cover some or all of the portion of the outer surface of the implant 95 that faces radially inward, away from the central longitudinal axis of the implant 95. For example, the second metal 182 can cover most or substantially all of such inward-facing surface of the implant 95, or most or substantially all of such inward-facing surface of the implant 95. In various embodiments, the second metal can cover at least 50%, at least 60%, at least 75%, at least 90%, at least 95%, or at least 98% of any such inward-facing surface of the implant 95. Additionally or alternatively, substantially all of such inward-facing surface of the implant 95 can be covered collectively by the second metal 182 in some areas and by some material other than the first metal 180 in other areas. In combination with any of the foregoing, the first metal 180 can cover, prevail in or be exposed in some or all of the portion of the outer surface of the implant 95 that faces radially outward, toward the central longitudinal axis of the implant 95. In some of the embodiments under discussion in this paragraph, the first metal can prevail substantially only on the outward-facing surface, and the second metal can prevail substantially only on the inward-facing surface, of the implant 95. In some embodiments, at least 50%, at least 60%, at least 75%, at least 90%, at least 95%, or at least 98% of a total surface area of the second metal can be at the inward-facing surface of the implant 95. In some embodiments, at least 50%, at least 60%, at least 75%, at least 90%, at least 95%, or at least 98% of a total surface area of the first metal can be at the outward-facing surface of the implant 95. In some embodiments, the first metal can be substantially absent from the inward-facing surface, and/or the second metal can be substantially absent from the outward-facing surface, of the implant 95. In some embodiments, less than 50%, less than 40%, less than 25%, less than 10%, less than 5%, or less than 2% of a total surface area of the second metal can be at the outward-facing surface of the implant 95. In some embodiments, at least 50%, at least 60%, at least 75%, at least 90%, at least 95%, or at least 98% of a total surface area of the second metal can be at other than the outward-facing surface of the implant 95. In some embodiments, less than 50%, less than 40%, less than 25%, less than 10%, less than 5%, or less than 2% of a total surface area of the first metal can be at the inward-facing surface of the implant 95. In some embodiments, at least 50%, at least 60%, at least 75%, at least 90%, at least 95%, or at least 98% of a total surface area of the first metal can be at the other than the inward-facing surface of the implant 95.

The implant 95 can have an outward-facing surface that is purely or substantially purely cathodic or anodic, and an inward-facing surface that is purely or substantially of the opposite polarity. In some such embodiments, the outward-facing surface is purely or substantially purely anodic and the inward-facing surface is purely or substantially purely cathodic, by employing a second metal of, e.g., zinc or magnesium that covers all or substantially all of the outward-facing surface and a first metal of, e.g., nitinol that covers all or substantially all of the inward-facing surface. In some such embodiments, the inward-facing surface is purely or substantially purely anodic and the outward-facing surface is purely or substantially purely cathodic, by employing a second metal of, e.g., zinc or magnesium that covers all or substantially all of the inward-facing surface and a first metal of, e.g., nitinol that covers all or substantially all of the outward-facing surface. The first metal can comprise the structural metal of the implant 95. It may be useful to provide an outward-facing surface that is purely or substantially purely anodic, for example, to attract positively-charged thrombus and cause it to adhere to the outward-facing surface, where the thrombus may more likely to detach from the implant 95 during removal (in contrast to the interior of the implant). It may be useful to provide an inward-facing surface that is purely or substantially purely anodic, for example, to attract positively-charged thrombus and cause it to adhere to the inward-facing surface and/or to avoid attachment to the vessel wall.

As depicted in FIGS. 1C and 2A, some or all of the openings 116 can be open (e.g., uncovered). Separately or additionally, the implant 95 as a whole, or a portion thereof, can be uncovered. Some or all of the portion of the outer surface of the implant 95 that faces radially outward, away from the central longitudinal axis of the implant 95, can be uncovered such that the radially-outward-facing portion of the outer surface of the implant 95 can comprise, in whole or in part, a vessel-wall-contacting, catheter-contacting, or aneurysm-contacting surface. In some embodiments, such a vessel-wall-contacting catheter-contacting, or aneurysm-contacting surface can be partially or entirely metallic, comprising metals of the galvanic cell, for example one or both of the first metal 180 and the second metal 182. In some embodiments, such a vessel-wall-contacting, catheter-contacting, or aneurysm-contacting surface can be substantially or entirely free of one or more metals of the galvanic cell, for example one or both of cathodic metal (e.g., the first metal 180) or anodic metal (e.g., the second metal 182). In some embodiments, less than 50%, less than 40%, less than 25%, less than 10%, less than 5%, or less than 2% of a total surface area of the second metal can be at the vessel-wall-contacting, catheter-contacting, or aneurysm-contacting surface. In some embodiments, less than 50%, less than 40%, less than 25%, less than 10%, less than 5%, or less than 2% of a total surface area of the first metal can be at the vessel-wall-contacting, catheter-contacting, or aneurysm-contacting surface. It may be useful to provide an outward-facing surface or a vessel-wall-contacting catheter-contacting, or aneurysm-contacting surface that is substantially or entirely free of anodic metal (i) to facilitate delivery and/or retrieval by providing a lower displacement force between the implant 95 (or a portion thereof) and a catheter, as compared to a force that would be required if the an outward-facing surface or a vessel-wall-contacting catheter-contacting, or thrombus-contacting surface comprised anodic metal, (ii) to protect the anodic metal from disruption, e.g., shearing, that might occur from sliding contact between the anodic metal and the catheter, or both.

Figure 11:
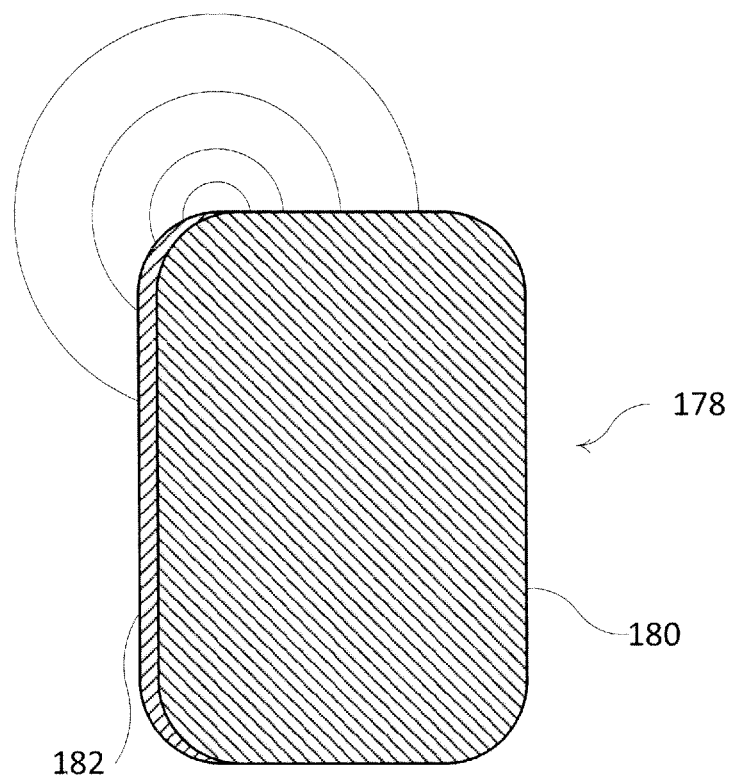
Figure 12:
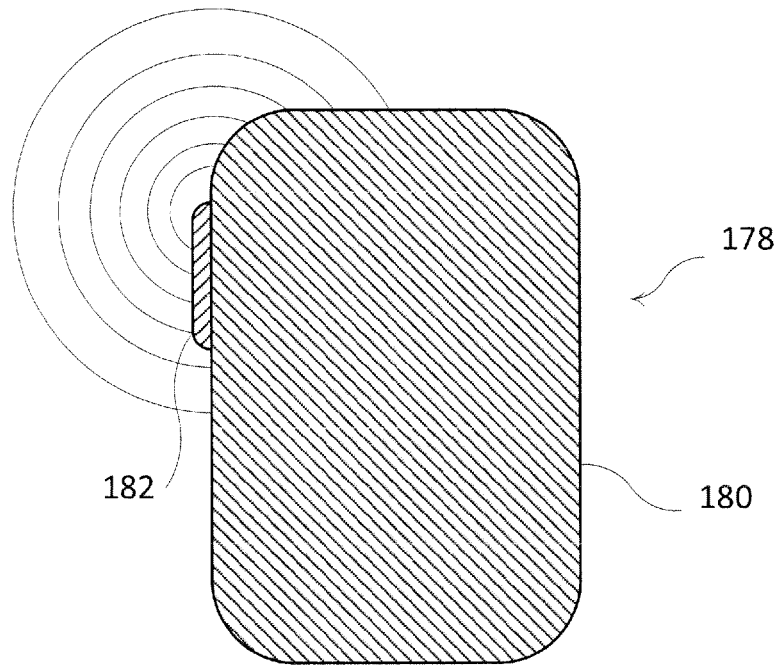

The ratio of anode surface area to cathode surface area affects the density of the generated current and the rate of the galvanic reaction. As the area of the anode becomes smaller compared to the cathode area, the current density increases and the reaction rate increases. Consider, for example, the filaments 178 shown in schematic cross-sections in FIGS. 11 and 12. As the galvanic cell of FIG. 11 has a higher ratio of anodic to cathodic surface area, it would generate a lower charge density and have a slower corrosion rate in the galvanic cell of FIG. 12. In a galvanic cell of the implant 95, the anodic metal can form from about 35% or about 45% to about 75% or about 85% of a total surface area of the galvanic cell. In the galvanic cells of some embodiments, the anodic metal can form about 35%, about 45%, about 55%, about 65%, about 75%, or about 85% of a total surface area of the galvanic cell.

The thickness of the anode affects the total reaction time of the galvanic cell. In some embodiments, the thickness of the anode is selected to provide 1-5, 5-10, 10-15, 15-20, 20-25, or 25-30 minutes of reaction time. In further embodiments, the thickness of the anode can be selected to provide 5-10 minutes of reaction time after positioning the implant 95 in a blood vessel. In some embodiments wherein the anode comprises magnesium and the cathode comprises nitinol, a magnesium thickness of about 2 to 3 micrometers can provide at least about five minutes of reaction time, e.g. where the anode:cathode area ratio is about 1:1. The thickness of the anodic metal may vary over a region of its coverage. For example, when the anodic metal is applied to a structural material by vapor deposition, the anodic metal may be thicker, as measured in a direction normal to the receiving surface, in regions oriented directly toward the direction of deposition than other regions.

Some or all of the implant 95 can be covered by a thin, dissolvable covering 188 (see FIGS. 8 and 10), e.g., film, that delays electrical activity of the galvanic cell until an amount of time has passed in the presence of a solvent, which may be a constituent of blood. For example, a dissolvable covering can isolate the implant from the blood until it dissolves, allowing the user to position or otherwise manipulate the expandable member before a galvanic reaction occurs. The dissolvable covering can cover some or all of the mesh, the proximal portion 122, the distal portion 176, the contacting portion of the outer surface of the expandable member in the overlap zones, or a combination thereof. The film can comprise a bioabsorbable polymer, for example, polylactic or polyglycolic acid, or a sugar, wax, oil, etc. The dissolvable covering can have a low coefficient of friction of contact with itself and a material forming an inner wall of a catheter, to facilitate delivery and deployment of the expandable member.

Figure 13:
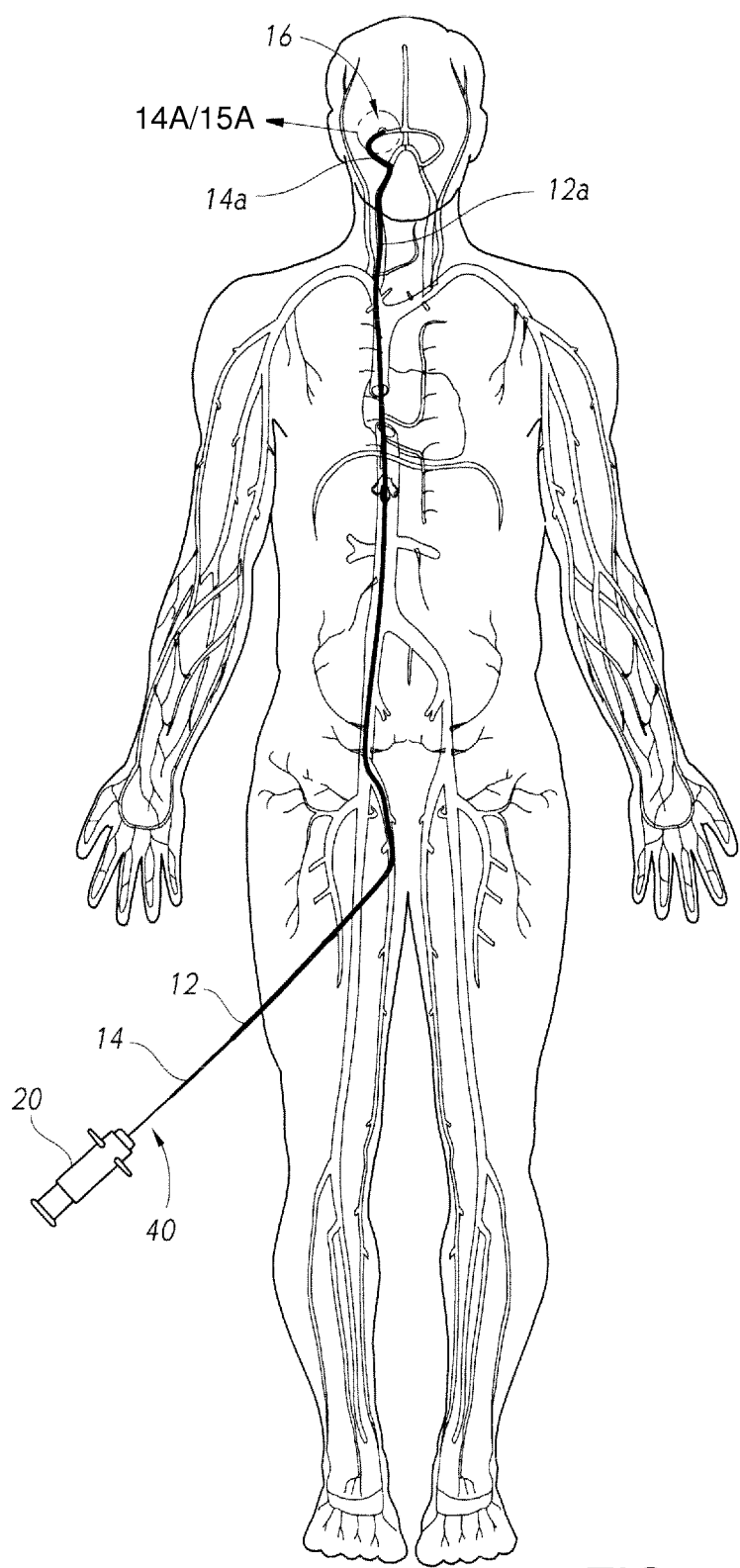
FIG. 13 shows a plan view of a position system within the human body.

FIG. 13 shows the positioning system 10 of FIGS. 1A-1B used inside a patient's vasculature. In the embodiment shown in FIG. 13, an operator uses a guide tube or guide catheter 12 to position a delivery tube or microcatheter 14 in a patient's vasculature. This procedure involves inserting the guide catheter 12 into the patient's vasculature through an access point such as the groin, and directing the distal portion 12a of the guide catheter 12 through the vascular system until it reaches the carotid artery. After removing a guide wire (not shown) from the guide catheter 12, a microcatheter 14 may be inserted into the guide catheter 12 and the distal portion 14a of the microcatheter 14 subsequently exits the guide catheter distal portion 12a and may be positioned near the target site 16, such as an aneurysm in the patient's brain.

Figure 14A:
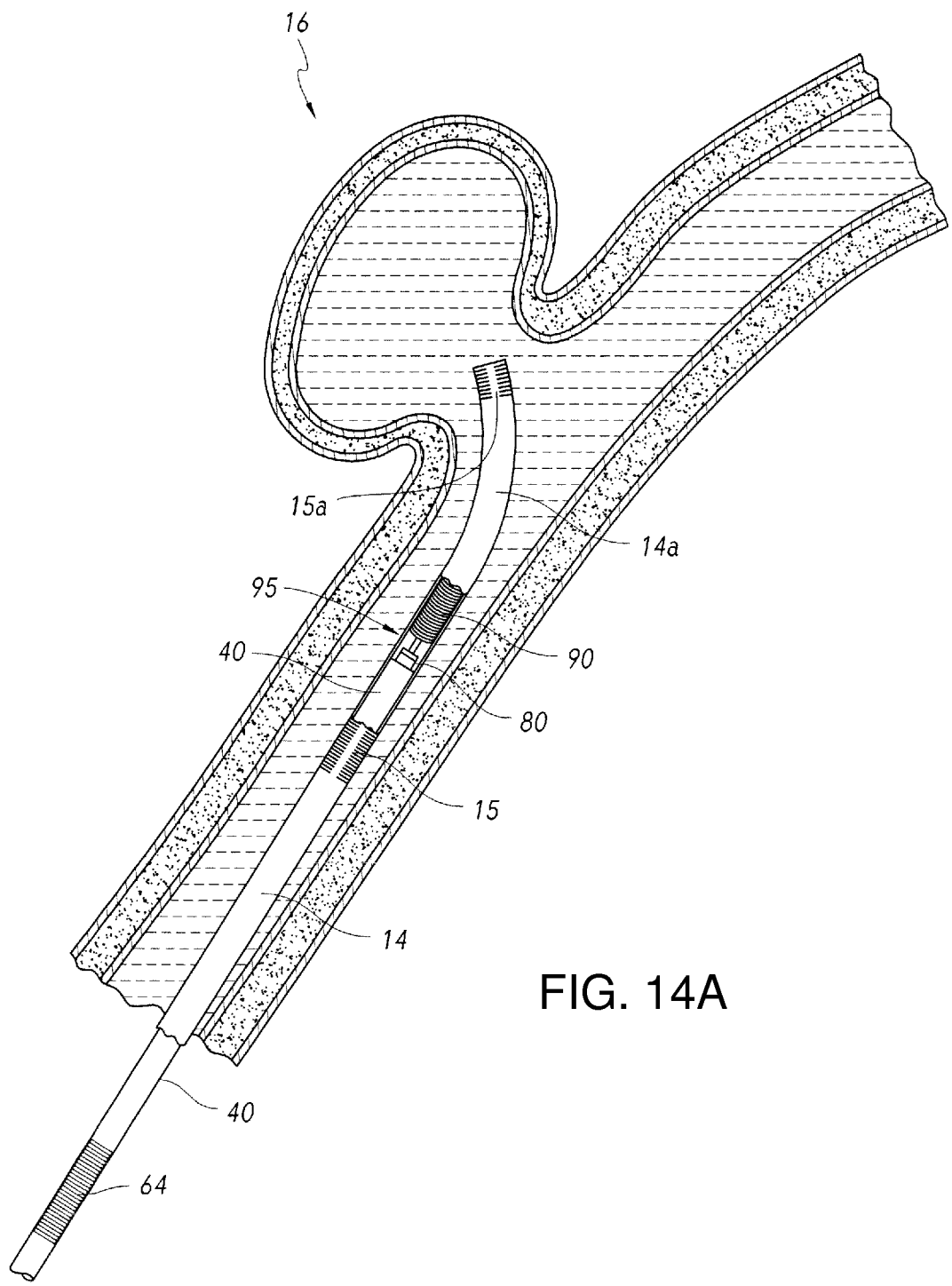
FIG. 14A shows a view of an exemplary portion of FIG. 13 showing the positioning system in partial cross-section and an exemplary coil in accordance with some embodiments of the subject technology in a position within the human body.
Figure 14B:
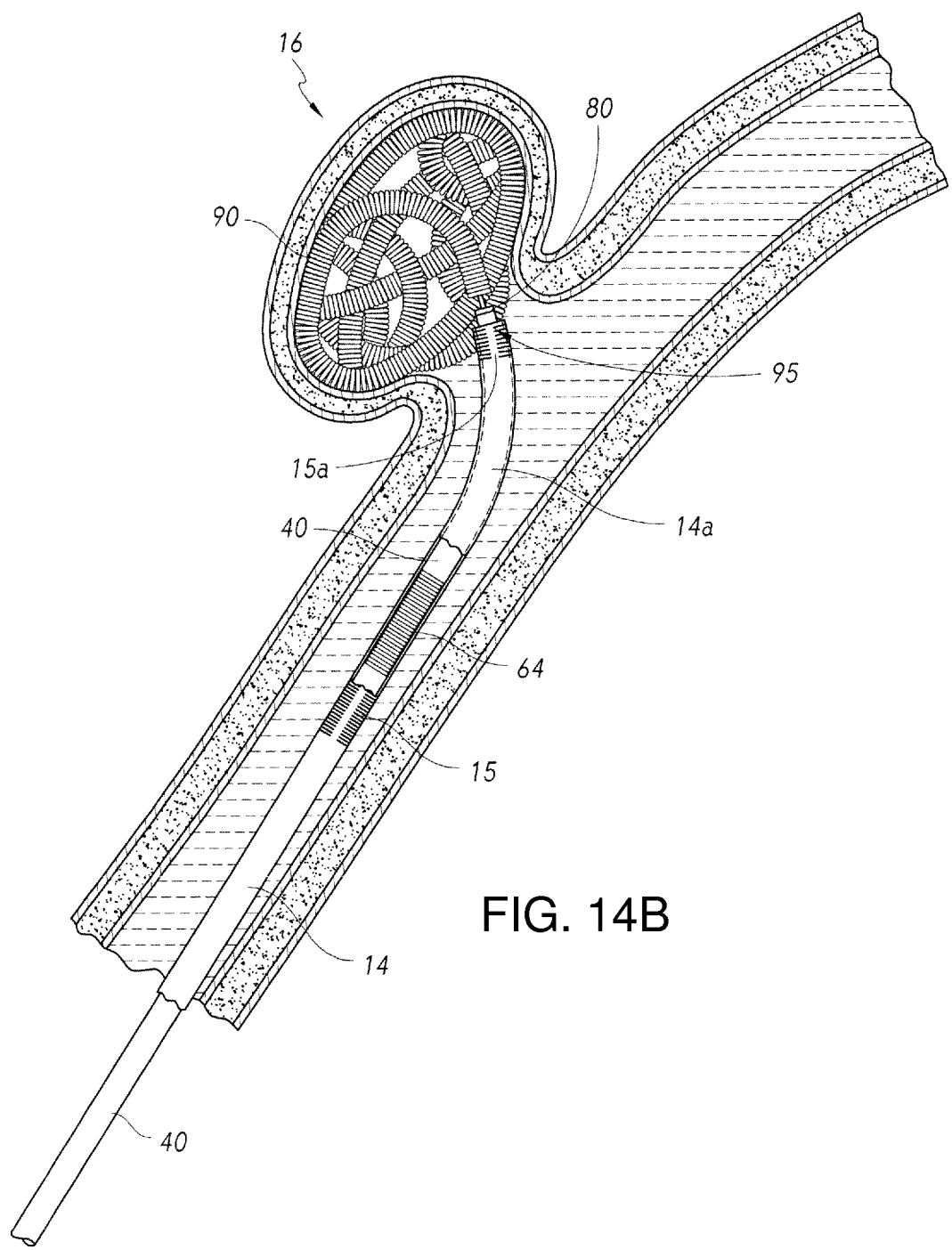
FIG. 14B shows a view of an exemplary portion of FIG. 13 showing the positioning system in partial cross-section and an exemplary coil in accordance with some embodiments of the subject technology in another position within the human body.
Figure 14C:
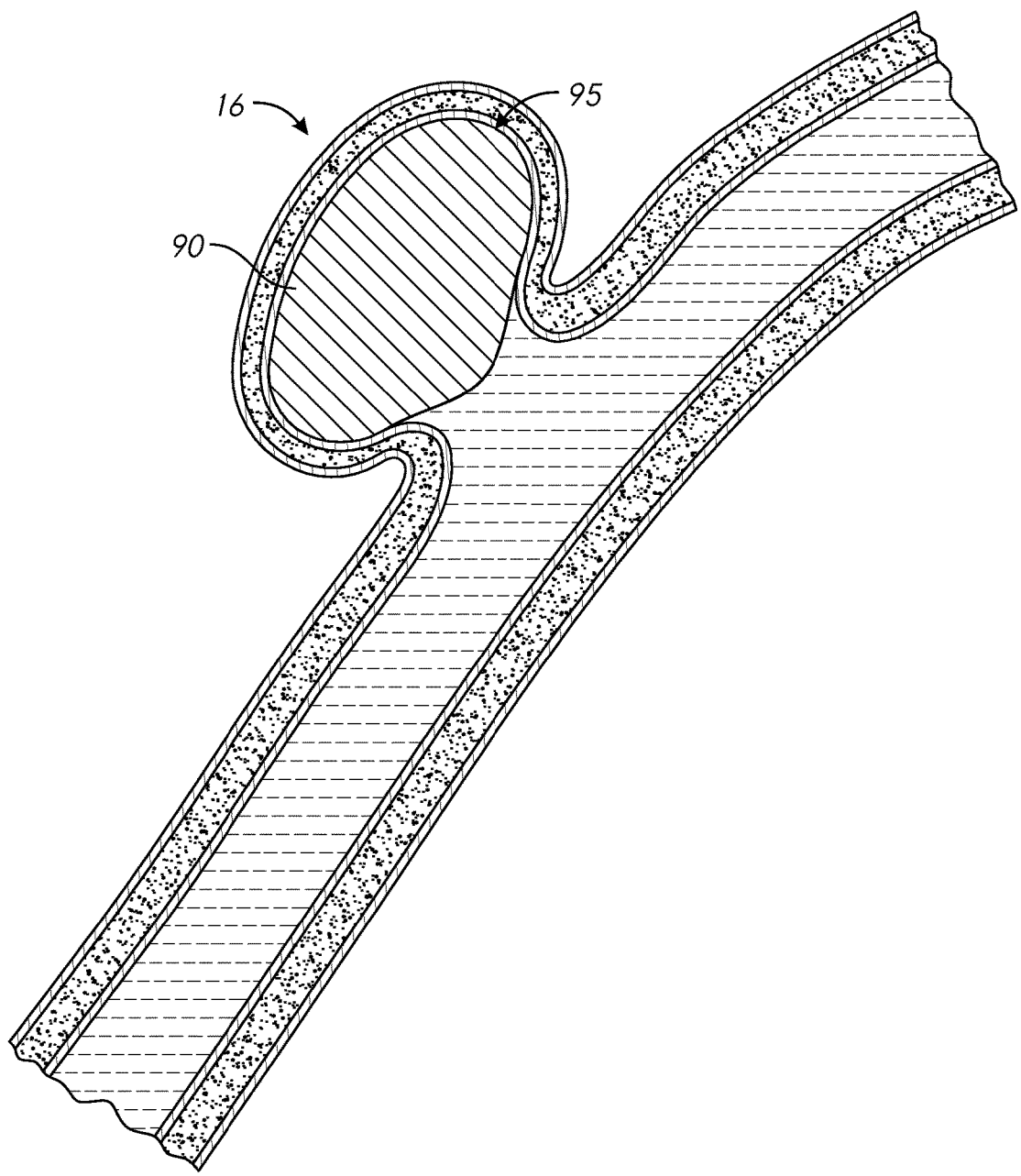
FIG. 14C shows a view of an exemplary portion of FIG. 13 showing the positioning system in partial cross-section and an exemplary coil in accordance with some embodiments of the subject technology with substantial thrombosis within the target site of the human body.

According to some embodiments, as shown in FIGS. 14A-14C, the positioning system 10 can be used to deliver an implant 95 such as or including a coil 90. In the embodiments illustrated in FIGS. 14A-14B, the microcatheter 14 can include microcatheter markers 15 and 15a that facilitate imaging of the distal portion 14a of the microcatheter 14 with common imaging systems. After the distal portion 14a reaches the target site 16, the positioning system 10 of the illustrated embodiment is then inserted into the microcatheter 14 to position the implant interface 80 at the distal portion of the positioner 40 near the target site 16, as illustrated in FIG. 14A. The coil 90 can be attached to the implant interface 80 prior to inserting the positioning system 10 into the microcatheter 14. The delivery of the coil 90 is facilitated by disposing the microcatheter marker 15a near the target site 16, and aligning the microcatheter marker 15 with a positioner marker 64 in the positioner 40 which, when the two markers (markers 15 and 64) are aligned with each other as illustrated in FIG. 14B, indicates to the operator that the implant interface 80 is in the proper position for the release of the coil 90 from the positioning system 10.

According to some embodiments, positioning the coil 90 within an aneurysm at the target site 16 can initiate a galvanic reaction that facilitates thrombosis at the target site 16. As shown in FIG. 14C, an interior body of the aneurysm may undergo progressive thrombosis and substantially stop flow of blood within the aneurysm.

According to some embodiments, substantial thrombosis can be achieved within a time period corresponding to a duration of a galvanic reaction. According to some embodiments, substantial thrombosis can be achieved after a time period corresponding to a duration of a galvanic reaction. A galvanic reaction can accelerate thrombosis such that substantial thrombosis is fully achieved even after the galvanic reaction has terminated.

According to some embodiments, substantial thrombosis can be more readily achieved within an aneurysm at the target site 16 through galvanic reactions provided by the coil 90. Where certain conditions relating to the coil 90 are required to achieve substantial thrombosis without galvanic reactions, such requirements can be alleviated by the galvanic activity disclosed herein. For example, where a given packing density is required to achieve substantial thrombosis without galvanic reactions, a lower packing density can be sufficient when accompanied by the galvanic activity of the subject technology. By further example, where a given number of coils are required to achieve substantial thrombosis without galvanic reactions, a smaller number of coils can be sufficient when accompanied by the galvanic activity of the subject technology. Such provisions can significantly reduce the cost and complexity of implants and procedures to achieve substantial thrombosis.

Figure 15A:
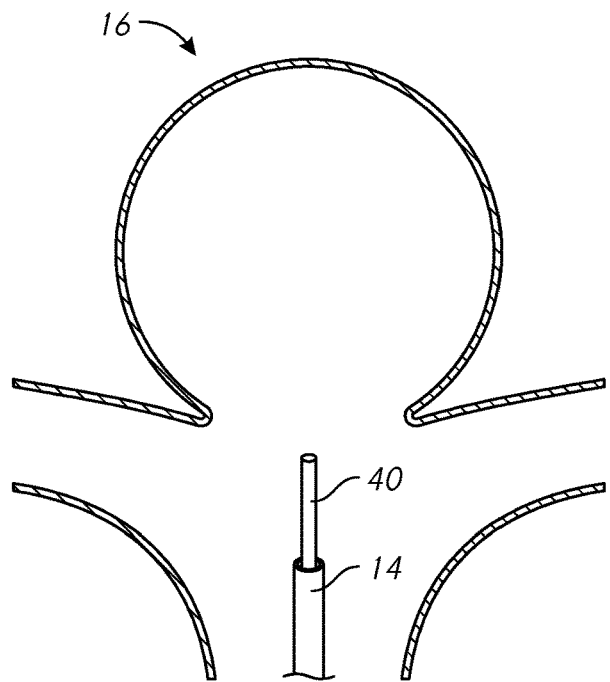
FIG. 15A shows a view of another exemplary portion of FIG. 13 showing the positioning system in partial cross-section and an exemplary braid ball in accordance with some embodiments of the subject technology in a position within the human body.
Figure 15B:
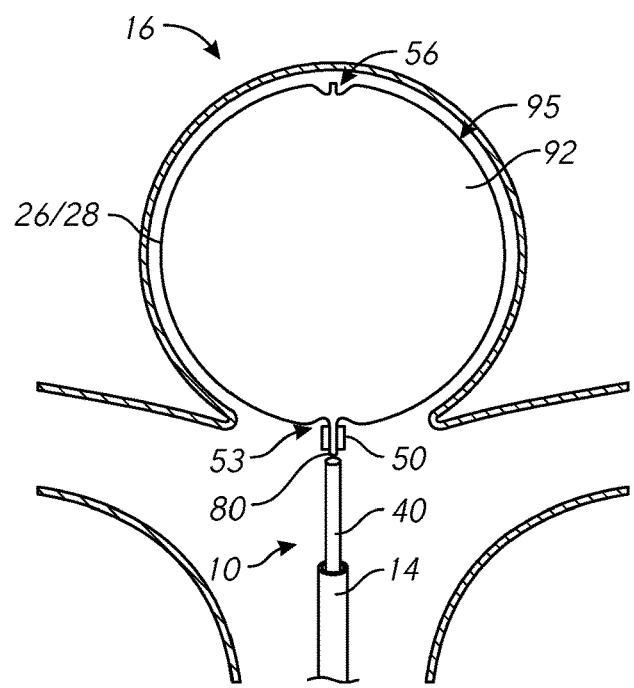
FIG. 15B shows a view of another exemplary portion of FIG. 13 showing the positioning system in partial cross-section and an exemplary braid ball in accordance with some embodiments of the subject technology in another position within the human body.
Figure 15C:
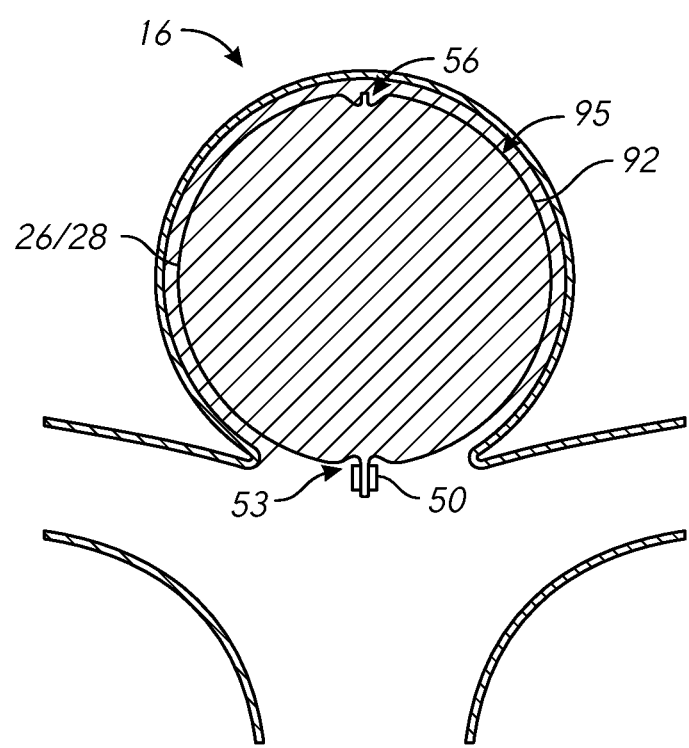
FIG. 15C shows a view of an exemplary portion of FIG. 13 showing the positioning system in partial cross-section and an exemplary braid ball in accordance with some embodiments of the subject technology with substantial thrombosis within the target site of the human body.

According to some embodiments, as shown in FIGS. 15A-15C, the positioning system 10 can be used to deliver an implant 95 such as or including a braid ball 92. The braid ball 92 can be delivered by a microcatheter with a delivery system as detailed below. To deliver the braid ball 92, the positioner 40 can be positioned such that the braid ball 92 can be delivered at least partially into the aneurysm sac at the target site 16, as shown in FIG. 15A-15B. After final positioning is achieved as shown in FIG. 15B, the braid ball 92 is released to remain within the aneurysm. Finally, the positioner 40 can be withdrawn into the microcatheter 14.

According to some embodiments, positioning the braid ball 92 within the aneurysm at the target site 16 can initiate a galvanic reaction that facilitates thrombosis at the target site 16. As shown in FIG. 15C, an interior body of the aneurysm may undergo progressive thrombosis and substantially stop flow of blood within the aneurysm. According to some embodiments, galvanic activity on or near a proximal portion 53 of the braid ball 92 can facilitate rapid thrombosis at the ostium of the aneurysm to reduce or prevent flow into or out of the aneurysm. Subsequently, further thrombosis within the aneurysm can be accelerated once flow has ceased and the blood remains stagnant. According to some embodiments, or multiple layers of the braid ball 92 are present at the proximal section 53, one, some, or all of the layers at the proximal section 53 can form one or more galvanic cells to promote galvanic activity and thrombosis.

According to some embodiments, substantial thrombosis can be more readily achieved within an aneurysm at the target site 16 through galvanic reactions provided by the braid ball 92. Where certain conditions relating to the braid ball 92 are required to achieve substantial thrombosis without galvanic reactions, such requirements can be alleviated by the galvanic activity disclosed herein. For example, where a given braid density is required to achieve substantial thrombosis without galvanic reactions, a lower braid density can be sufficient when accompanied by the galvanic activity of the subject technology. By further example, where a given number of layers of the braid ball 92 are required to achieve substantial thrombosis without galvanic reactions, a smaller number of layers can be sufficient when accompanied by the galvanic activity of the subject technology. Such provisions can significantly reduce the cost and complexity of implants and procedures to achieve substantial thrombosis.

EXAMPLES

An investigation was performed to verify duration and magnitude of galvanic cell operation based on various anodic metal thicknesses. Several 7 mm×7 mm square nitinol samples with various thickness of PVD-deposited Mg coatings (Isoflux, Inc.) were tested in saline. Magnesium coating thicknesses of 0.25, 0.5, 0.75, 1.0, 2.0, and 3.0 microns thick were evaluated. Samples were attached (on the NiTi side) to an insulative post and placed into saline, and the time for the surface to turn black in color (i.e., "time to oxidize") due to the oxidation reaction was recorded. Reactions continued at slower rates after the Mg surface turned fully black, and the black coating then began to separate from the substrate until almost completely off. The EMF galvanic voltage for Mg—NiTi is 1.3 volts. In this test situation, the anode is the Mg coating, and the cathode is the NiTi substrate. As the area of the anode becomes smaller compared to the cathode area, the current density increases and the reaction rate increases. The 7×7 mm NiTi squares, coated with PVD Mg, produces an approximate ratio of about 0.5 (50%). Results are shown below in Table 1:

TABLE 1

| Sample | Mg thickness (μm) | Reaction temperature (° C.) | Time to oxidize (minutes) |
|---|---|---|---|
| 1 | 0.25 | 22 | 1.0 |
| 2 | 0.25 | 22 | 0.75 |
| 3 | 0.5 | 22 | <2.0 |
| 4 | 0.5 | 22 | 1.5 |
| 5 | 0.75 | 22 | <2.5 |
| 6 | 0.75 | 22 | 1.5 |
| 7 | 1.0 | 22 | 4.0 |
| 8 | 1.0 | 22 | 2.5 |
| 9 | 1.0 | 22 | 2.75 |
| 10 | 1.0 | 37 | 1.8 |
| 11 | 2.0 | 22 | 9.0 |
| 12 | 2.0 | 22 | 11.25 |
| 13 | 2.0 | 22 | 12.0 |
| 14 | 2.0 | 22 | 3.4 |
| 15 | 2.0 | 37 | 5.8 |
| 16 | 3.0 | 22 | 18.0 |
| 17 | 3.0 | 22 | 11.5 |
| 18 | 3.0 | 22 | 8.4 |
| 19 | 3.0 | 37 | 9.5 |
| 20 | 3.0 | 22 | 13.3 |

For each thickness, the above results were averaged to provide the results shown below in Table 2:

TABLE 2

| Mg thickness (μm) | Average time to oxidize (minutes) |
|---|---|
| 0.25 | 0.9 |
| 0.5 | 1.8 |
| 0.75 | 2.0 |
| 1 | 3.1 |
| 2 | 8.9 |
| 3 | 12.8 |

Additionally, a platinum (Pt) coil with a 5.5 micron Mg coating on the outer surface thereof was tested. Only a "line-of-sight" region of the coil outer surface was coated with Mg on one side thereof (e.g., see FIG. 7). The coating was non-uniform due to the curvature of the coil geometry. Thus, the anode/cathode ratio for the coils was on the order of 0.1 or less. The EMF galvanic voltage for the Pt—Mg couple was 1.7 volts. In this test, the anode is the Mg coating, and the cathode is the Pt coil. Results are shown below in Table 3:

TABLE 3

| Mg thickness (μm) | Reaction temperature (° C.) | Time to oxidize (minutes) |
|---|---|---|
| 5.5 | 22 | 2.0 |

As can be seen, the thickness of the anode metal contributes to the duration of the galvanic reaction. Accordingly, a duration of galvanic activity can be controlled based on the thickness of the anode metal provided to a cathode metal at a time of production. Based on the results above, a thickness of anodic material can be selected based on a desired duration of galvanic activity. Those having skill in the art will recognize that a variety of material pairings and thicknesses can be provided to achieve the desired results. The thickness of anodic material can remain small enough to avoid substantial interference with a heat set or shape memory configuration of the implant 95. For example, a layer of anodic material after the implant 95 has been heat set into a particular configuration will have little impact on the implants ability to recover that configuration.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A medical device comprising:
    a primary structure including a structural cathodic metal and an anodic metal coated on a portion of the structural cathodic metal, the structural cathodic metal being in direct contact with the anodic metal, the anodic metal and the structural cathodic metal each forming a fraction of a total surface area of the primary structure;
    wherein the primary structure comprises a braided ball or helical coil configured to be implanted within an aneurysm within a body to occlude blood flow and promote thrombosis within the aneurysm,
    wherein a thickness of the anodic metal is less than or equal to 5 μm, and a galvanic cell formed by the anodic metal and the structural cathodic metal is configured to induce a galvanic voltage within blood within the body for between 5 and 30 minutes, and wherein the primary structure is configured such that, after oxidation of the anodic metal is complete, the structural cathodic metal remains physically intact.

2. The intrasaccular medical device of claim 1, further comprising a temporary cover material that encapsulates at least a portion of the anodic metal.

3. The intrasaccular medical device of claim 2, wherein the temporary cover material is erodible, dissolvable, degradable or absorbable in vivo.

4. The intrasaccular medical device of claim 3, wherein the temporary cover material encapsulates substantially all of the anodic metal.

5. The intrasaccular medical device of claim 1, wherein the primary structure forms a helical coil.

6. The intrasaccular medical device of claim 5, further comprising:
 a stretch-resistant member extending within a lumen formed by the helical coil; and
 at least one fiber attached to the helical coil and extending outwardly from a central axis of the helical coil.

7. The intrasaccular medical device of claim 1, wherein the fraction of the surface area formed by the anodic metal is located primarily at an internal aspect of the implant.

8. The intrasaccular medical device of claim 1, wherein 35% to 85% of the surface area of the primary structure is formed by the anodic metal.

9. The intrasaccular medical device of claim 1, wherein the fraction of the total surface area formed by the anodic metal comprises a plurality of discrete portions of the anodic metal.

10. The intrasaccular medical device of claim 1, wherein the fraction of the surface area formed by the anodic metal is contiguous.

11. The intrasaccular medical device of claim 1, wherein at least a portion of the anodic metal has a thickness of at least 1 µm.

12. The intrasaccular medical device of claim 1, wherein the anodic metal comprises magnesium and the cathodic metal comprises nickel and titanium.

13. The intrasaccular medical device of claim 1, wherein the primary structure forms a braided ball.

14. The intrasaccular medical device of claim 1, wherein the galvanic cell is configured to induce a galvanic voltage within blood within the body for between 5 and 30 minutes, and no longer.

15. A medical device comprising:
 a primary structure configured to occupy a space within the aneurysm, the primary structure comprising a structural cathodic metal and an anodic metal deposited directly onto the structural cathodic metal such that the structural metal is in direct contact with the anodic metal, wherein the primary structure comprises a braided ball or helical coil configured to be implanted with an aneurysm within a body to occlude blood flow and promote thrombosis within the aneurysm;
 means for inducing a galvanic voltage between the anodic metal and the structural cathodic metal of the primary structure while within blood of the body, to galvanically assist thrombosis within the body for between 5 and 30 minutes,
 wherein the primary structure is configured such that, after the galvanic voltage is induced for between 5 and 30 minutes, the structural cathodic metal remains physically intact.

16. The intrasaccular medical device of claim 15, wherein the means for galvanically assisting thrombosis within the body comprises the anodic metal and the structural cathodic metal.

17. The intrasaccular medical device of claim 16, wherein a thickness of the anodic metal is less than or equal to 5 µm.

18. The intrasaccular medical device of claim 16, wherein the anodic metal comprises magnesium and the structural cathodic metal comprises nickel and titanium.

19. The intrasaccular medical device of claim 15, wherein said means comprises means for inducing a galvanic voltage between the anodic metal and the structural cathodic metal of the primary structure while within blood of the body, to galvanically assist thrombosis within the body for between 5 and 30 minutes, and no longer.

20. A method, comprising:
 inserting an implantable intrasaccular medical device into an aneurysm within a body to occlude blood flow and promote thrombosis within the aneurysm, the medical device comprising:
  a primary structure including a structural cathodic metal and an anodic metal coated on a portion of the structural cathodic metal, the structural cathodic metal being in direct contact with the anodic metal, the anodic metal and the structural cathodic metal each forming a fraction of a total surface area of the primary structure, wherein a thickness of the anodic metal is less than or equal to 5 µm, and wherein the primary structure comprises a braided ball or helical coil;
 galvanically assisting thrombosis within the space with a galvanic cell formed by the anodic metal and the structural cathodic metal by inducing a galvanic voltage within blood within the body for between 5 and 30 minutes,
 wherein, after oxidation of the anodic metal is complete, the structural cathodic metal remains physically intact.

21. The method of claim 20, wherein the galvanic cell is activated while the implantable medical device is within the aneurysm within the body.

22. The method of claim 20, wherein galvanically assisting thrombosis comprises binding, through a galvanic reaction, blood constituents to an anode of the galvanic cell.

23. The method of claim 20, wherein inducing a galvanic voltage within blood within the body for between 5 and 30 minutes, comprises doing so for between 5 and 30 minutes, and no longer.

* * * * *

UNITED STATES PATENT AND TRADEMARK OFFICE
CERTIFICATE OF CORRECTION

PATENT NO. : 10,265,515 B2
APPLICATION NO. : 14/671217
DATED : April 23, 2019
INVENTOR(S) : James Davidson Page 1 of 1

It is certified that error appears in the above-identified patent and that said Letters Patent is hereby corrected as shown below:

In the Claims

In Column 19, Claim 2, Line 6, delete "intrasaccular";
In Column 19, Claim 3, Line 9, delete "intrasaccular";
In Column 19, Claim 4, Line 13, delete "intrasaccular";
In Column 19, Claim 5, Line 16, delete "intrasaccular";
In Column 19, Claim 6, Line 18, delete "intrasaccular";
In Column 19, Claim 7, Line 24, delete "intrasaccular";
In Column 19, Claim 7, Line 26, delete "implant" and insert --primary structure--;
In Column 19, Claim 8, Line 27, delete "intrasaccular";
In Column 19, Claim 9, Line 30, delete "intrasaccular";
In Column 19, Claim 10, Line 34, delete "intrasaccular";
In Column 19, Claim 11, Line 37, delete "intrasaccular";
In Column 19, Claim 12, Line 40, delete "intrasaccular";
In Column 19, Claim 13, Line 43, delete "intrasaccular";
In Column 19, Claim 14, Line 45, delete "intrasaccular";
In Column 20, Claim 16, Line 10, delete "intrasaccular";
In Column 20, Claim 17, Line 14, delete "intrasaccular";
In Column 20, Claim 18, Line 16, delete "intrasaccular";
In Column 20, Claim 19, Line 19, delete "intrasaccular"; and
In Column 20, Claim 20, Line 40, delete "space" and insert --body--.

Signed and Sealed this
Fifth Day of November, 2019

Andrei Iancu
*Director of the United States Patent and Trademark Office*